US 11,809,011 B2

(12) United States Patent
Yang et al.

(10) Patent No.: US 11,809,011 B2
(45) Date of Patent: Nov. 7, 2023

(54) ALIGNMENT METHOD AND TOOLS

(71) Applicant: Boston Scientific Scimed, Inc., Maple Grove, MN (US)

(72) Inventors: Xirong Yang, Fremont, CA (US); Baocheng Yang, Fremont, CA (US); Brian Cheng, San Jose, CA (US); Peter Bull, San Jose, CA (US); Viju Panicker, San Jose, CA (US); Yang-Te Fan, Cupertino, CA (US); Rongwei Jason Xuan, Fremont, CA (US); Thomas Charles Hasenberg, Campbell, CA (US); Jian James Zhang, Lancaster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 134 days.

(21) Appl. No.: 17/643,858

(22) Filed: Dec. 13, 2021

(65) Prior Publication Data

US 2022/0206239 A1 Jun. 30, 2022

Related U.S. Application Data

(60) Provisional application No. 63/131,162, filed on Dec. 28, 2020.

(51) Int. Cl.
*G02B 7/00* (2021.01)
*G02B 27/10* (2006.01)
(Continued)

(52) U.S. Cl.
CPC ........... *G02B 7/003* (2013.01); *G02B 27/106* (2013.01); *G02B 27/14* (2013.01); *H01S 3/061* (2013.01);
(Continued)

(58) Field of Classification Search
CPC ...... G02B 7/003; G02B 27/106; G02B 27/14; H01S 3/061; H01S 3/092; H01S 3/161;
(Continued)

(56) References Cited

U.S. PATENT DOCUMENTS

2017/0027756 A1 2/2017 Angeley et al.
2018/0366896 A1 12/2018 Yu
(Continued)

FOREIGN PATENT DOCUMENTS

WO WO-2010021529 A2 * 2/2010 ............. H01S 5/141

OTHER PUBLICATIONS

International Search Report issued in International Application No. PCT/US2021/072869 dated Apr. 19, 2022 (10 pages).

*Primary Examiner* — William Choi
(74) *Attorney, Agent, or Firm* — Seager, Tufte & Wickhem, LLP

(57) ABSTRACT

A laser system includes a first laser cavity to output a laser light along a first path, a first mirror to receive the laser light from the first laser cavity, and redirect the laser light along a second path that is different than the first path, a second mirror to receive the laser light from the first mirror, and redirect the laser light along a third path that is different than the first path and the second path, a beam splitter located at a first position on the third path, a beam combiner located at a second position on the third path; and a coupling lens assembly, the coupling lens assembly including a lens located at a third position on the third path, wherein the coupling lens assembly moves the lens in x-, y-, and x-directions.

20 Claims, 9 Drawing Sheets

(51) Int. Cl.
  *G02B 27/14* (2006.01)
  *H01S 3/06* (2006.01)
  *A61B 18/20* (2006.01)
  *H01S 3/092* (2006.01)
  *H01S 3/16* (2006.01)

(52) U.S. Cl.
  CPC ............... *A61B 18/20* (2013.01); *H01S 3/092* (2013.01); *H01S 3/161* (2013.01); *H01S 3/1616* (2013.01); *H01S 3/1623* (2013.01); *H01S 3/1643* (2013.01)

(58) Field of Classification Search
  CPC .... H01S 3/1616; H01S 3/1623; H01S 3/1643; A61B 18/20
  USPC .......................................................... 359/618
  See application file for complete search history.

(56) References Cited

U.S. PATENT DOCUMENTS

2019/0146226 A1    5/2019   Yu
2019/0353857 A1   11/2019   Ishikawa et al.
2020/0222118 A1    7/2020   Yu et al.

\* cited by examiner

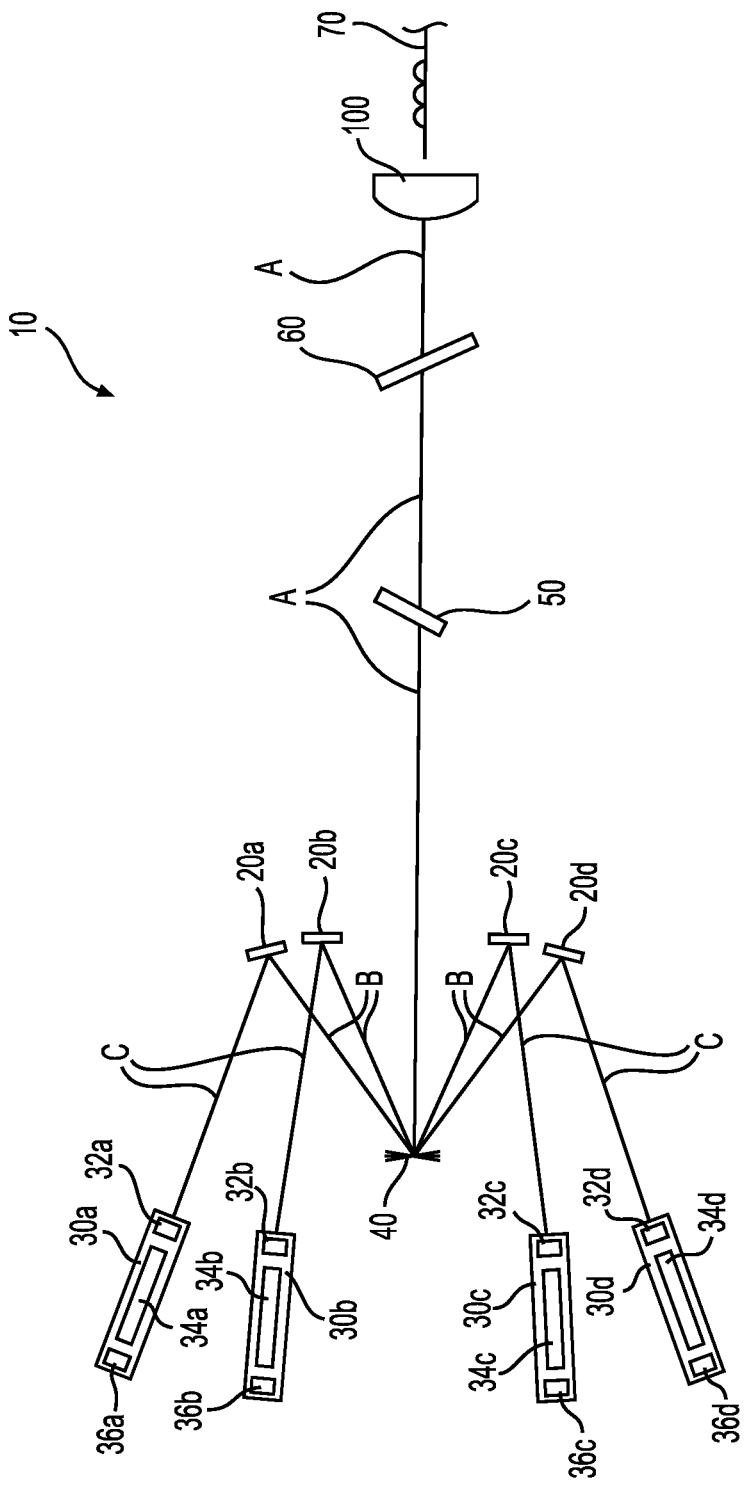

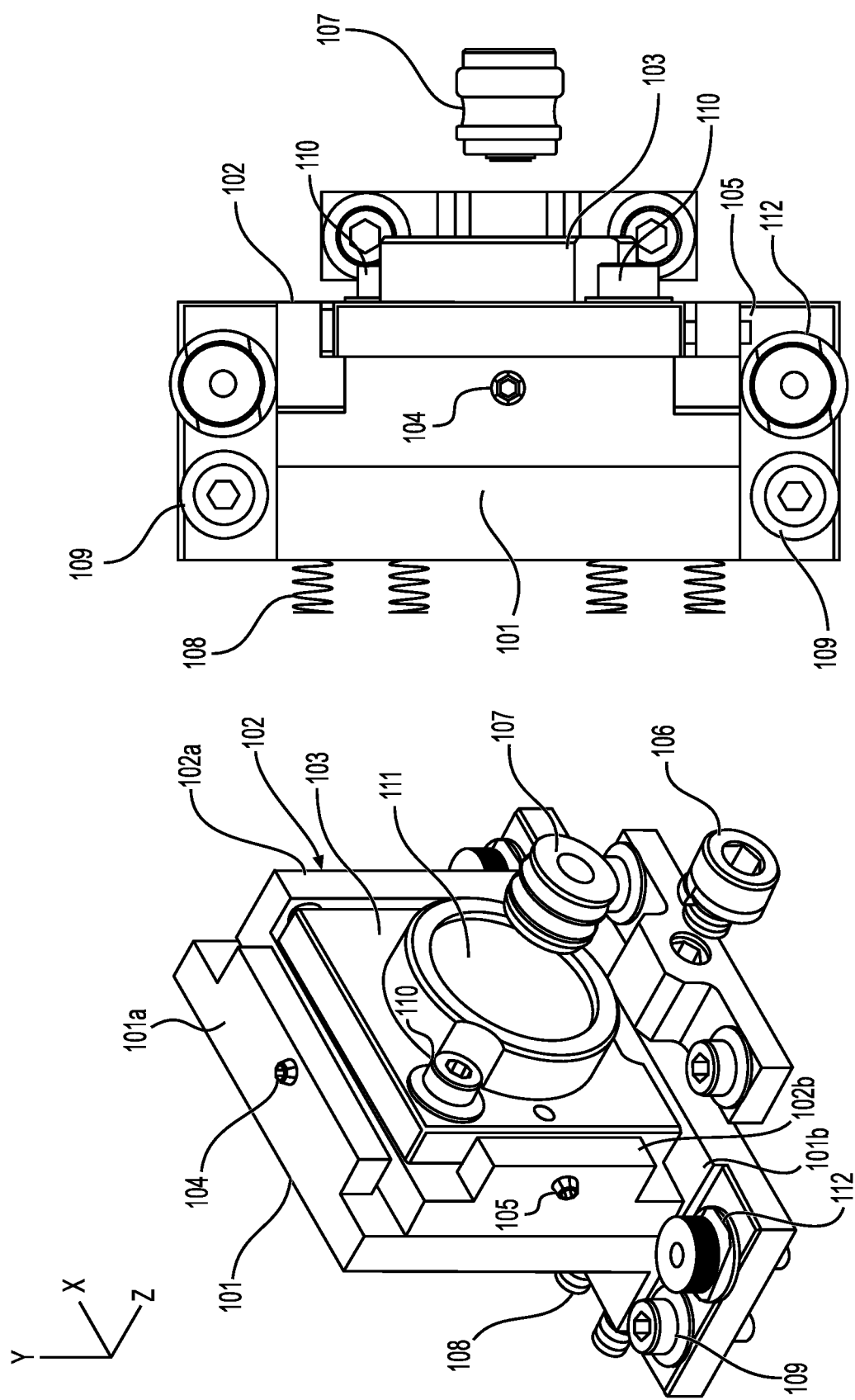

ALIGNMENT METHOD AND TOOLS

CROSS-REFERENCE TO RELATED APPLICATIONS

This patent application claims the benefit of priority under 35 U.S.C. § 119 to U.S. Provisional Patent Application No. 63/131,162, filed Dec. 28, 2020, which is herein incorporated by reference in its entirety.

TECHNICAL FIELD

The present disclosure relates generally to medical/surgical laser systems, and more particularly, to methods and tools for aligning the medical/surgical laser systems.

BACKGROUND

Medical laser systems are used for a variety of surgical procedures. These procedures may include dusting and/or fragmentation of stones in the kidney, the bladder, and/or the ureter. Medical laser systems are also used to create incisions and to ablate and/or coagulate soft tissues, such as, but not limited to, the prostate. Surgical lasers output from medical laser systems have small laser pulse wavelengths, e.g., approximately 2 µm, and are invisible to the naked eye, e.g., medical lasers having mid-infrared wavelengths. Thus, it is necessary to use a visible alignment laser beam to align the medical laser system.

Conventional alignment procedures for medical laser systems are time consuming, with alignment of laser cavities and/or mirrors generally taking about one to two days to complete. One problem with conventional alignment techniques results from the use of laser pulses generated from the laser cavities, which has safety risks and which can cause damage to optics. Another problem associated with conventional alignment techniques is the use of a thermal paper during alignment. The use of thermal paper is necessary for these conventional systems since the alignment is not accurate, and thermal paper aids in correcting this accuracy. When the output beam is shot through the thermal paper, however, particles are generated which can contaminate and cause damage to the optics.

SUMMARY OF THE DISCLOSURE

According to an aspect, a laser system includes a first laser cavity configured to output a laser light along a first path, a first mirror configured to receive the laser light from the first laser cavity, and redirect the laser light along a second path that is different than the first path, a second mirror configured to receive the laser light from the first mirror, and redirect the laser light along a third path that is different than the first path and the second path, a beam splitter located at a first position on the third path, a beam combiner located at a second position on the third path, and a coupling lens assembly, the coupling lens assembly including a lens located at a third position on the third path, wherein the coupling lens assembly is configured to move the lens in x-, y-, and z-directions.

The coupling lens assembly may include an outer housing configured to house a base frame, a stage plate, and a lens holder configured to support the lens, wherein the base frame, the stage plate, and the lens holder may move relative to each other.

The stage plate may include a pair of sidewalls, wherein a portion of the lens holder may be disposed between the pair of sidewalls, and wherein the lens holder may move toward one and the other of the pair of sidewalls.

The base frame may include a top wall and a bottom, wherein a portion of the stage plate may be disposed between the top wall and the bottom wall, and wherein the stage plate may move toward one and the other of the top wall and the bottom wall.

The laser system may further include a plurality of screw members to move the base frame, the stage plate, and the lens holder.

The laser system may further include at least one biasing member to bias the stage plate in a distal direction.

The laser system may further include a plurality of locking members to lock a position of the base frame, the stage plate, and the lens holder.

The base frame, the stage plate, and the lens holder may move independently.

The laser system may further include a plurality of first alignment members, wherein each of the plurality of first alignment members may include an opening, and wherein one first alignment member from the plurality of first alignment members may be disposed on the third path distal to the second mirror, and wherein another first alignment member from the plurality of first alignment members may be disposed on the third path proximal to the second mirror.

The laser system may further include an aiming laser generator, wherein the aiming laser generator may deliver an aiming laser to the beam combiner, wherein a portion of the aiming laser may pass through the beam combiner along a fourth path, and wherein the aiming laser generator may be aligned when the aiming laser passes through the opening in at least two first alignment members from the plurality of first alignment members arranged on the fourth path.

The laser system may further include a pair of second alignment members, each of the second alignment members may have an opening, wherein each of the second alignment members may be attached to the first laser cavity on the first path.

A laser generating rod may be removed from the first laser cavity before the second alignment members are attached to the first laser cavity.

The laser generating rod may be disposed on a first longitudinal axis when the laser generating rod may be attached to the first laser cavity, and wherein the opening in each of the second alignment members may be disposed on the first longitudinal axis.

The laser system may further include an output fiber to deliver a laser energy from the laser system to a target.

An alignment laser beam may be directed into the laser system from a distalmost end of the third path.

According to another aspect, a method for aligning a laser system includes delivering an alignment beam through a lens, wherein the lens is supported by a coupling lens assembly, and adjusting the coupling lens assembly to move the lens in an x-, y-, and z-direction such that the alignment beam passes through an opening in a first alignment feature positioned at a first location and through an opening in a second alignment feature positioned at a second location, onto a first mirror contained within the laser system.

The method may further include removing a laser rod from a laser cavity of the laser system, attaching a third alignment feature and a fourth alignment feature to the laser cavity, wherein each of the third alignment feature and the fourth alignment feature may include an opening, removing one of the first or second alignment features from the laser system, and adjusting one or more of the first mirror, a second mirror, and a third mirror such that the alignment beam passes through the openings in both the third alignment feature and the fourth alignment feature, onto a fourth mirror at a proximal end of the laser cavity.

The method may further include adjusting the third mirror, located at a distal end of the laser cavity, and the fourth mirror such that the aiming beam is reflected from the fourth mirror through the opening in one of the third alignment feature or the fourth alignment feature.

According to yet another aspect, a method for aligning a laser system having a first laser cavity includes delivering an aiming into the laser system via a lens, wherein the lens is supported by a coupling lens assembly, moving the lens in one or more of the x-, y-, or z-directions such that the aiming laser impinges on a first mirror, and moving the first mirror, a second mirror, and a third mirror such that the aiming laser beam passes through openings in a plurality of alignment devices and impinges on a fourth mirror at a proximal end of a laser cavity.

The method may further include delivering a second aiming laser to the laser system onto a coupler, wherein a first portion of the aiming light passes through the coupler along a first path, and wherein a second portion of the aiming light, different from the first portion, is reflected by the coupler along a second path adjusting a position of the aiming laser such that the first portion of the aiming light passes through openings in a pair of alignment devices disposed along the first path.

BRIEF DESCRIPTION OF THE DRAWINGS

The accompanying drawings, which are incorporated in and constitute a part of this specification, illustrate various exemplary embodiments and, together with the description, serve to explain the principles of the disclosed embodiments.

FIG. 1 is a schematic of a medical laser system according to an exemplary embodiment;

FIGS. 2A, 2B, and 2C are views of a coupling lens assembly according to an exemplary embodiment;

DETAILED DESCRIPTION

Figure 2A:
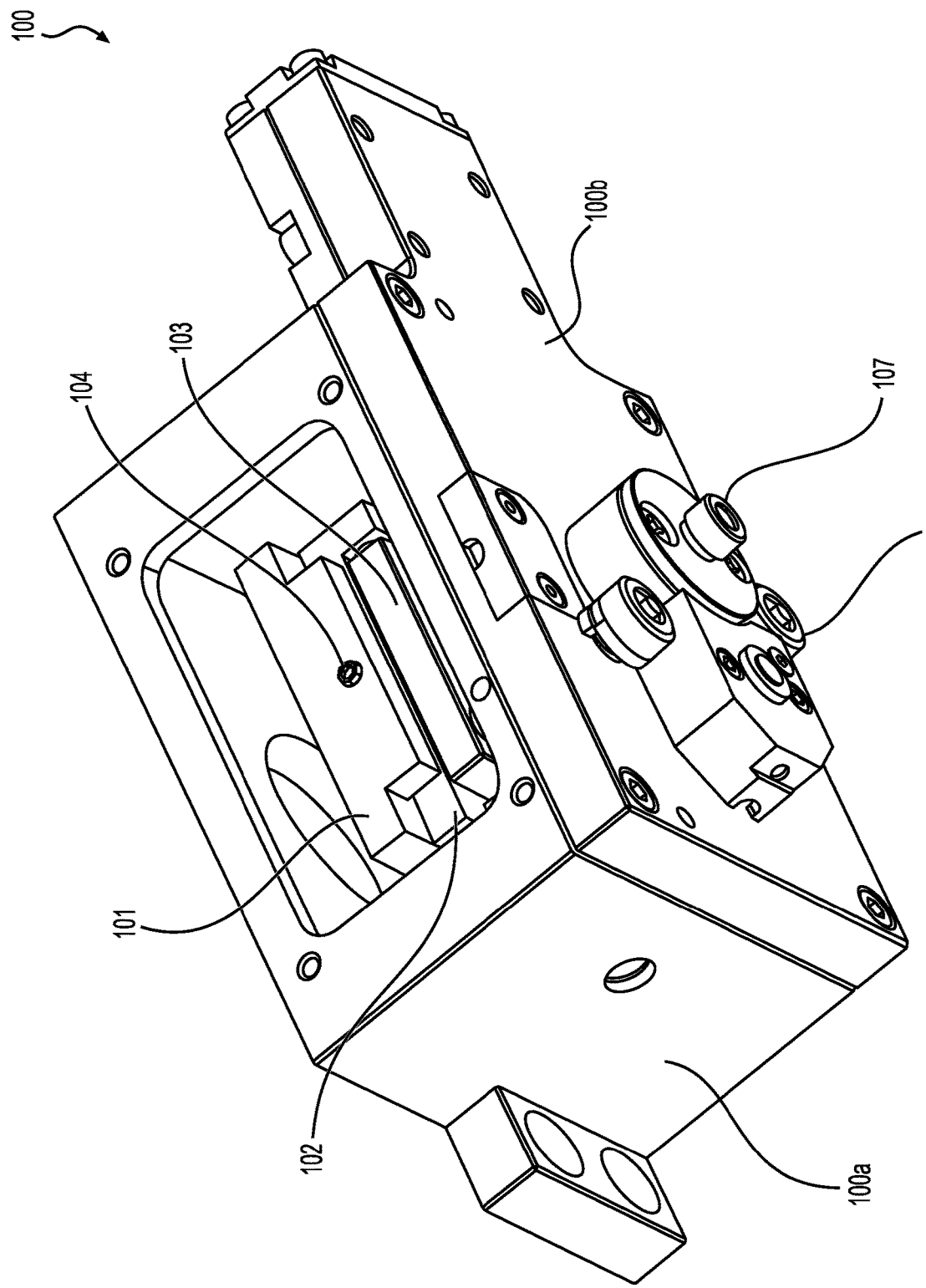

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

For ease of description, portions of the disclosed devices and/or their components are referred to as proximal and distal portions. It should be noted that the term "proximal" is intended to refer to portions closer to laser cavities of the laser device, and the term "distal" is used herein to refer to portions further away from the laser cavities of the laser device, e.g., toward an end of a laser fiber that outputs a laser energy. Similarly, extends "distally" indicates that a component extends in a distal direction, and extends "proximally" indicates that a component extends in a proximal direction. Additionally, terms that indicate the geometric shape of a component/surface refer to exact and approximate shapes.

FIG. 1 illustrates an exemplary embodiment of a medical laser system 10. The medical laser system 10 includes one or more laser cavities 30a-30d (one laser cavity 30 shown in FIGS. 3A and 3B), each laser cavity capable of outputting an output laser beam (or laser light). Each of the one or more laser cavities 30a-30d includes a high reflecting window 36a-36d at a proximal end, an output coupler window 32a-32d at a distal end, and a chromium thulium holmium-doped YAG (CTH:YAG) laser rod 34a-34d disposed between respective high reflecting windows 36a-36d and output coupler window 32a-32d. CTH:YAG lasers are lamp-pumped (flash-lamp-pumped) Ho:YAG lasers, having a pulse width in the range of approximates 100 microseconds to approximately 2-3 milliseconds. Wavelengths of the lasers are approximately 2.14 µm, and may have a highest pulse energy of greater than 5 Joules at a pulse width of one millisecond. CTH:YAG lasers may be efficiently operated at a repetition rate at less than or equal to approximately 25 Hertz, with a maximum average power for each laser cavity being approximately 30 Watts. To ablate tissue and create a high enough heat to destroy objects, such as kidney stones, it is necessary to increase the repetition rate by using multiple laser cavities, each laser cavity having a CTH:YAG laser rod (e.g., 34a-34d). Combining laser energy generated from each laser cavity may provide an overall repetition rate of up to approximately 80 Hertz, and an average maximum power of greater than 100 Watts. Ensuring the laser energy generated from each laser cavity is coupled into the fiber and reaches the target tissue facilitates generating these high-power outputs. Thus, it is important to properly align the laser cavities, mirrors, and other elements as described herein.

Each CTH:YAG laser rod 34a-34d generates an output laser beam for each of the cavities 30a-30d, which is directed to a corresponding relay mirror 20a-20d (e.g., first mirrors) along a laser path C. For example, the output laser beam is output from cavity 30a to mirror 20a; from cavity 30b to mirror 20b; from cavity 30c to mirror 20c; and from cavity 30d to mirror 20d, with each output laser beam traveling along corresponding laser paths C. Each output laser beam is reflected from a respective one of the relay mirrors 20a-20d to a Galvo mirror 40 (e.g., second mirror) along respective laser paths B. For example, an output laser beam is reflected from relay mirror 20a to Galvo mirror 40 along laser path B. Galvo mirror 40 reflects each output laser beam along a same optical path A (e.g., laser path A) to a beam splitter 50 and a beam combiner 60. Galvo mirror 40 is configured to rotate about an axis to face each of relay mirrors 20a-20d and receive output lasers from each laser cavity 30a-30d. The beam combiner 60 combines the output laser beams from the one or more cavities 30a-30d and may further combine an aiming beam from an aiming beam source (e.g., an aiming beam source 701 in FIG. 7). The combined laser beam is passed along laser path A to a coupling lens 111 of coupling lens assembly 100 (FIG. 2B). The coupling lens 111 couples the output laser beam and matches the output laser beam to an output fiber 70, to be transmitted to a delivery location. Coupling lens 111 may be any material suitable for coupling the laser light to output fiber 70, including but not limited to a sapphire. Coupling lens 111 may have a diameter of approximately 18 mm, but is not limited thereto.

To help ensure proper output and to help avoid damage to the medical laser system 10, and injuries to the user and/or the patient, the medical laser system 10 may be calibrated prior to use. The calibration and alignment of the medical laser system 10 may help ensure that the output laser from the one or more laser cavities 30a-30d properly reflects off each mirror and are coupled through coupling lens 111 into the output fiber 70. After the alignment using the procedures described herein, fine-alignments of medical laser system 10 may be reduced to finalize the alignment. The alignment procedures of the present disclosure also may help technicians and operators service laser systems in the field, without requiring the systems to be sent off-site for service, and/or may reduce the time for calibrating medical laser systems 10 before delivering these systems to customers.

According to an exemplary embodiment, coupling lens assembly 100 may be configured to move coupling lens 111 in the x-, y-, and z-directions during the alignment procedures to ensure proper alignment of the out laser beam. As shown in FIG. 2A, coupling lens assembly 100 includes a housing 100a, 100b to house a base frame 101. Housing 100a, 100b may include a proximal-most portion 100a and a distalmost portion 100b connected via screws or other fastening devices. Proximal-most portion 100a may include a recess or cavity configured to receive base frame 101 and other elements of coupling lens assembly 100. Distalmost portion 100b may be attached to proximal-most portion 100a after base frame 101 is inserted into the cavity of proximal-most portion 100a, thereby fixing base frame 101 within the cavity of housing 100a, 100b. A fiber ferrule 107, which may attach to a proximal-most end of fiber 70 and which may connect fiber 70 to coupling lens assembly 100, may be attached to a distal end of housing 100a, 100b. Fiber ferrule 107 may connect to a connector of fiber 70, such as an SMA connector or other similar connector for connecting fiber 70 to coupling lens assembly 100.

With reference to FIGS. 2B and 2C, adjusting screws 104, 105, and 106 may cause elements of coupling lens assembly 100 to move, thereby causing coupling lens 111 to move in the x-, y-, and z-directions, respectively. The x-direction axis defines a horizontal direction, and the y-direction axis defines a vertical direction. Coupling lens 111 is generally circular in cross-section and is supported by a lens holder 103. It will be understood that coupling lens 111 may be any shape suitable for coupling the output laser to fiber 70. Lens holder 103 is generally rectangular in cross-section, but is not limited thereto. Lens holder 103 is disposed between two vertical walls 102a, 102b of a stage plate 102. Walls 102a, 102b extend in a vertical direction. One of vertical walls 102a, 102b includes adjusting screw 105. According to an example, adjusting screw 105 is provided within an opening of wall 102b and is configured to move relative to stage plate 102 along an x-axis. Adjusting screw 105 may move transverse to vertical walls 102a, 102b and may cause lens holder 103 to move relative to walls 102a, 102b, thereby moving lens 111 in the x-direction. For example, rotating adjusting screw 105 in a first direction (e.g., a clockwise direction) may cause lens holder 103 to move to the right along the x-axis, and rotating adjusting screw 105 in a second direction, opposite the first direction (e.g., a counterclockwise direction) may cause lens holder 103 to move to the left along the x-axis. Adjusting screw 105 may move the lens holder 103 (e.g., by pushing or pulling against lens holder 103 via a threaded connection), or adjusting screw 105 may cooperate with a biasing member (e.g., a spring), which may provide a biasing or urging force against lens holder 103 in a direction toward adjusting screw 105.

Stage plate 102 is disposed between two horizontal walls 101a, 101b of base frame 101. One of walls 101a, 101b includes adjusting screw 104. According to an example, adjusting screw 104 is provided within an opening of wall 101a and is configured to move relative to base frame 101 along a y-axis. Adjusting screw 104 may move transverse to horizontal walls 101a, 101b, and may cause stage plate 102 to move relative to walls 101a, 101b, thereby moving stage plate 102, lens holder 103, and lens 111 in the y-direction. For example, rotating adjusting screw 104 in a first direction (e.g., a clockwise direction) may cause stage plate 102 to move downwards along the y-axis, and rotating adjusting screw 104 in a second direction, opposite the first direction (e.g., a counterclockwise direction) may cause stage plate 102 to move to upwards along the y-axis. Adjusting screw 104 may move stage plate 102 directly (e.g., by pushing or pulling against stage plate 102 via a threaded connection), or adjusting screw 104 may cooperate with a biasing member (e.g., a spring), which may provide a biasing or urging force against stage plate in a direction toward adjusting screw 104.

Adjusting screw 106 and springs 108 (e.g., biasing members) may be used to position base frame 101 within housing 100a, 100b. Springs 108 may be positioned at a proximal end of base frame 101, and adjusting screw 106 may be positioned at a distal end of base frame 101. Springs 108 may urge or bias base frame 101 in a distal direction relative to housing 100a, 100b, and screw 106 may provide an opposing force in an opposite direction, i.e., in the proximal direction. Rotation of screw 106 may move screw 106 proximally and distally relative to housing 100a, 100b, which may allow base frame 101 to move proximally and distally (i.e., in the z-direction) relative to housing 100a, 100b. For example, rotating adjusting screw 106 in a first direction (e.g., a clockwise direction) may cause base frame 101 to move proximally along the z-axis, and rotating adjusting screw 106 in a second direction, opposite the first direction (e.g., a counterclockwise direction) may cause base frame 101 to move distally along the z-axis. Since base frame 101 is located within housing 100a, 100b, sidewalls of housing 100a, 100b may define a path along the z-axis along which base frame 101 may move, such that base frame 101 slides along the z-axis. Once the proper alignment of lens 111 is achieved, screws 109 and 110 may be tightened to maintain a position of 101, 102, and 103 within housing 100a, 100b. For example, screws 109 and 112 (FIG. 2C) may be provided on either side of base frame 101 in the x-direction and may secure a position of base frame 101 to housing 100a, 100b and/or a baseboard (not shown) of medical laser system 10. Screws 110 are provided at opposite corners on a distal end face of lens holder 103 and may secure a position of lens holder 103 to stage plate 102 once an appropriate position of lens holder 103 is achieved. It will be understood that screws 104, 105, 106, 109, and 110 may be operated by hand, e.g., using a thumb and a forefinger, and/or screws 104, 105, 106 may include a recess to receive a tool, such as an end of a screwdriver or similar tool to cause rotational movement of screws 104, 105, 106, 109, and 110 in their respective openings. The screw threads on each of screws 104, 105, 106, 109, and 110 may enable the rotational movement to result in translational movement of each screw 104, 105, 106, 109, and 110. It will be understood that the screws described herein may be any fastening mechanism such as thumb screws, clamps, or any other fastening mechanism not to one of ordinary skill in the art.

Figure 3B:
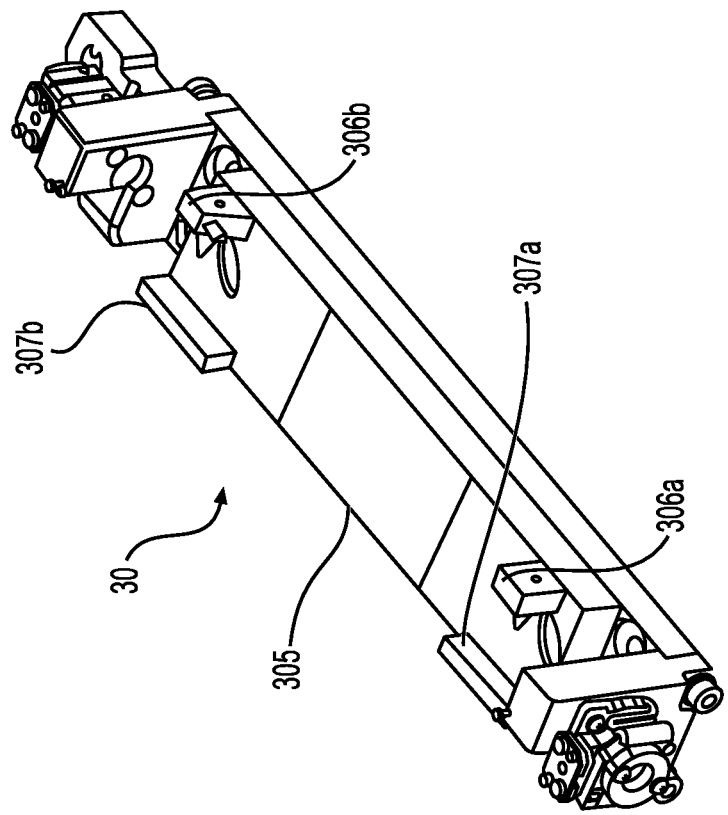
FIG. 3B is a perspective view of the laser cavity of FIG. 3A without a laser generating portion according to an exemplary embodiment.
Figure 3A:
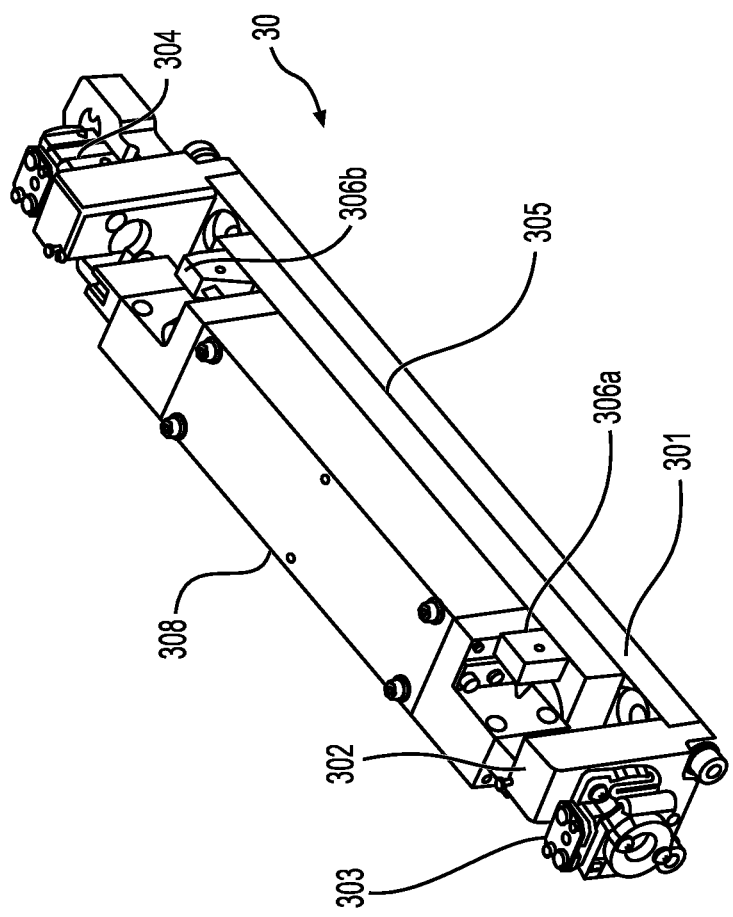
FIG. 3A is a perspective view of a laser cavity of the medical laser system of FIG. 1 according to an exemplary embodiment.

A laser cavity 30, which is an example of laser cavities 30a-30d, is illustrated in FIGS. 3A and 3B. Laser cavity 30 includes a base plate 301, a base 302 configured to support a mirror mount 303 for a reflecting window (e.g., reflecting windows 36a-36d of FIG. 1) at a first end of base plate 301, and a mirror mount 304 configured to support an output coupler window (e.g., output coupler 32a-32d of FIG. 1) at an opposite end of base plate 301. An insulating plate 305 may be positioned on a top surface of base plate 301 and between base 302 and mirror mount 304 in the proximal-distal direction. Proximal and distal end walls 306a, 306b, respectively, and sidewalls 307a, 307b may protrude from a top surface of insulating plate 305. Walls 306a, 306b, 307a, 307b may ensure proper positioning of a laser pumping chamber 308, which includes the CTH:YAG laser rod configured to generate each laser beam (e.g., laser rods 34a-34d in FIG. 1). Laser pumping chamber 308 may be secured to insulating plate 305 via screws at proximal and distal ends. Screw openings (not shown) in insulating plate 305 which receive the screws securing laser pumping chamber 308 to insulating plate 305 may also receive screws for securing second alignment devices 403 (see FIG. 5B). As shown in FIG. 3B, laser pumping chamber 308 may be removed during calibration to position second alignment devices 403 (see, FIG. 5B) as will be described herein.

Figure 4:
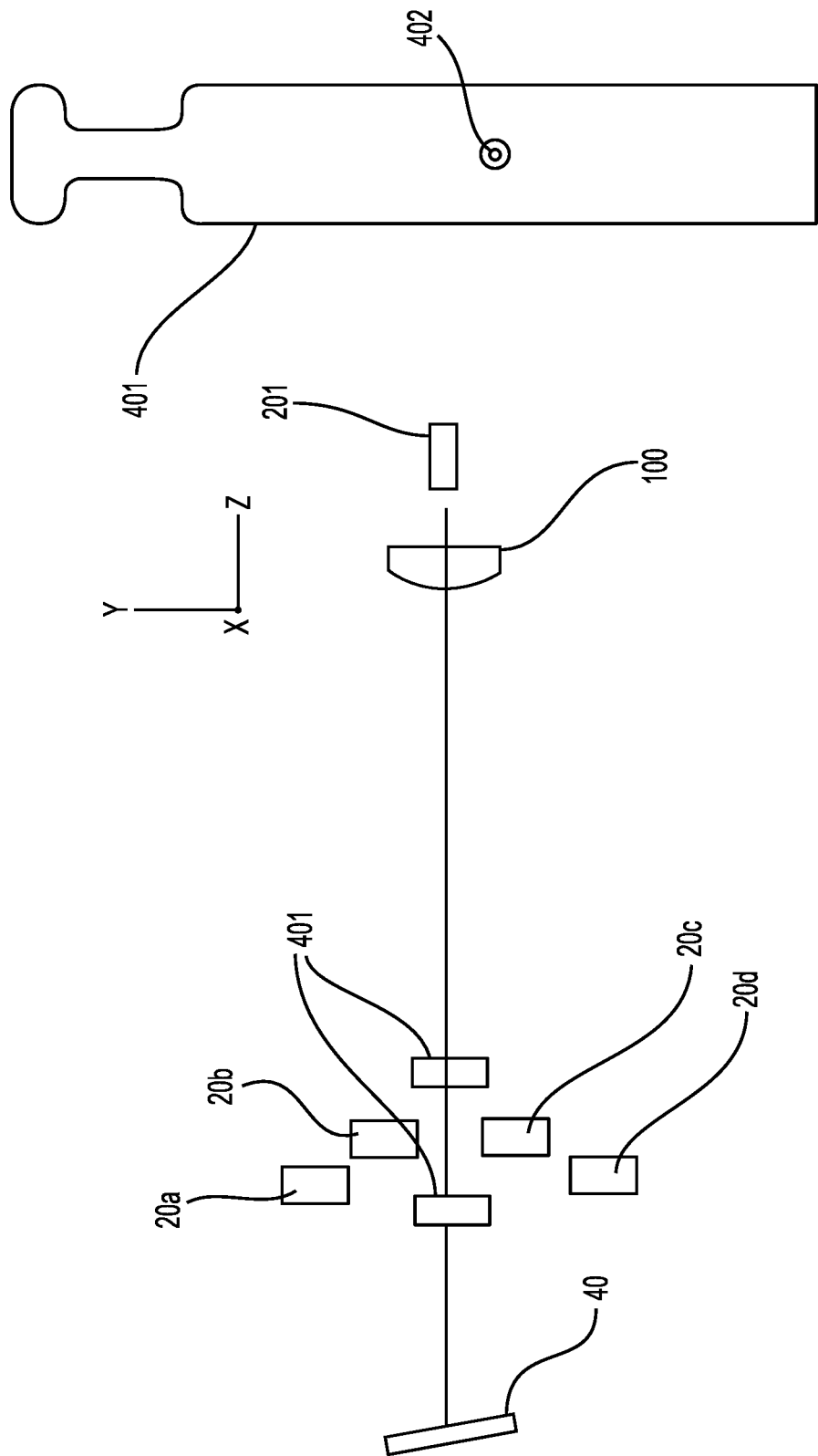
FIG. 4 is a front view of a first alignment device and a schematic of a first alignment procedure according to an exemplary embodiment.
Figure 6:
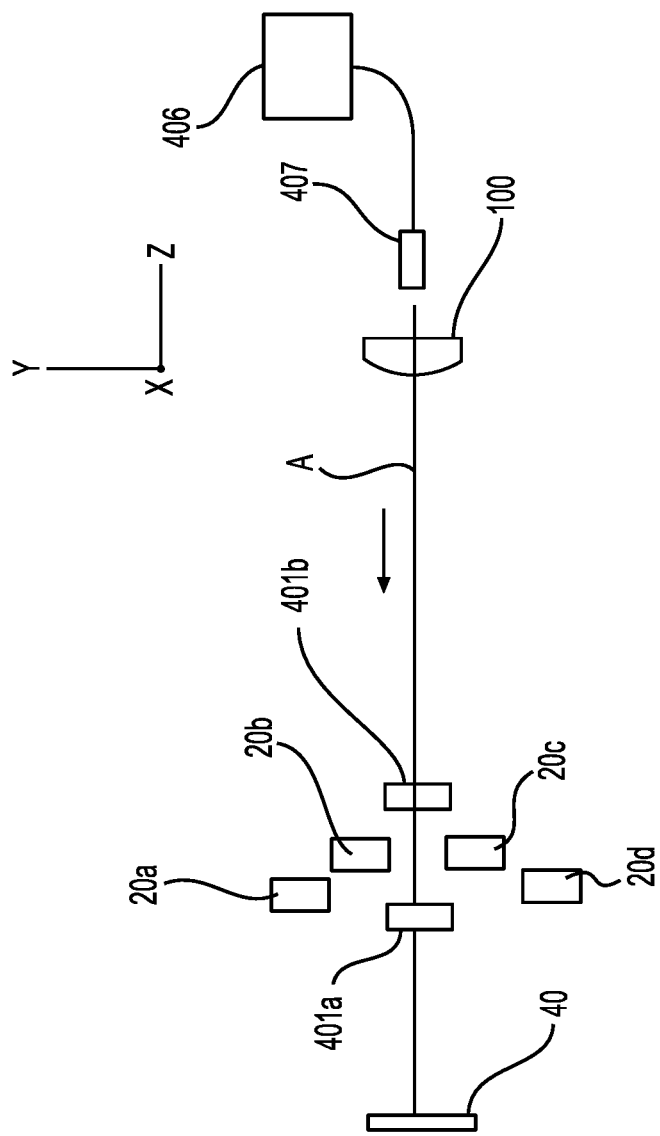
FIG. 6 is a schematic of a first alignment procedure according to an exemplary embodiment.

FIG. 4 illustrates a first alignment device 401 and an example position of first alignment device 401 (a proximal first alignment device 401a and a distal first alignment device 401b are shown in FIG. 6) for aligning medical laser system 10. First alignment device 401 may be an elongate member with a neck portion at one end (e.g., a top end as shown in FIG. 4). The neck portion may allow a user to grasp first alignment device 401 using a thumb and a forefinger and may also inform the user which end (i.e., the end opposite the neck portion) is to be attached to the baseboard (not shown) of medical laser system 10. An opening 402 is formed in first alignment device 401 and may allow laser light to pass therethrough during an alignment procedure. A diameter of opening 402 may be equal to or greater than approximately 1 millimeter (mm) and less than or equal to approximately 2 mm, and a center of opening 402 may be positioned approximately 35 mm to approximately 40 mm from a bottom end of alignment device 401, i.e., an end opposite the neck portion. In some examples, the center of opening 402 may be approximately 38.1 mm from the bottom end of alignment device 401. In some instances, a diameter of opening 402 in proximal first alignment device 401a may be different than a diameter of opening 402 in distal first alignment device 401b. The bottom end of first alignment device 401 may be attached to the baseboard (not shown) of medical laser system 10, to which Galvo mirror 40, relay mirrors 20a-20d, and other members of laser system 10 are secured. For example, proximal and distal first alignment devices 401a, 401b may be attached to the baseboard of medical laser system 10 along laser path A, as shown in FIG. 4. For example, distal first alignment device 401a may be positioned distally of relay mirrors 20a-20d, and proximal first alignment device 401b may be positioned proximally of relay mirrors 20a-20d, such that both the first and second alignment devices 401a, 401b are positioned along laser path A. An aiming laser beam may be directed into the medical laser system 10 along laser path A via, e.g., a connector 201 attached to coupling lens assembly 100. As will be described herein, the aiming beam may assist in aligning various elements, including mirrors, of medical laser system 10. Three types of fibers may be used for alignment, based on the type of fiber to which medical laser system 10 is to be coupled. For example, the core diameters of the three fibers is approximately 910 μm for a first fiber, approximately 365 μm for a second fiber, and approximately 273 μm for a third fiber. The concentricity of each core is within approximately 15 μm, or within approximately 10 μm of the design. The natural aperture (NA) of each fiber is approximately 0.22.

Figure 5A:
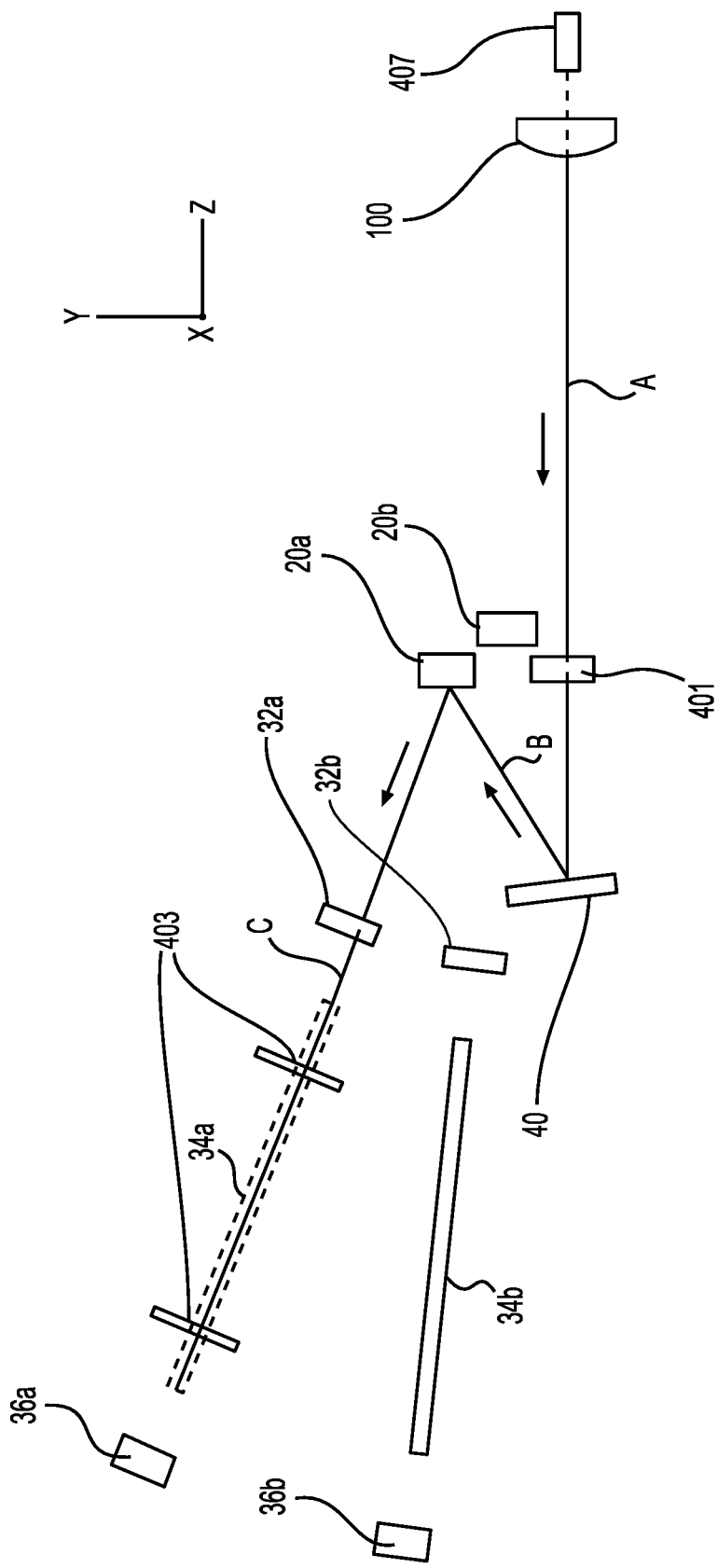
FIG. 5A is a schematic of a second alignment procedure according to an exemplary embodiment.
Figure 5B:
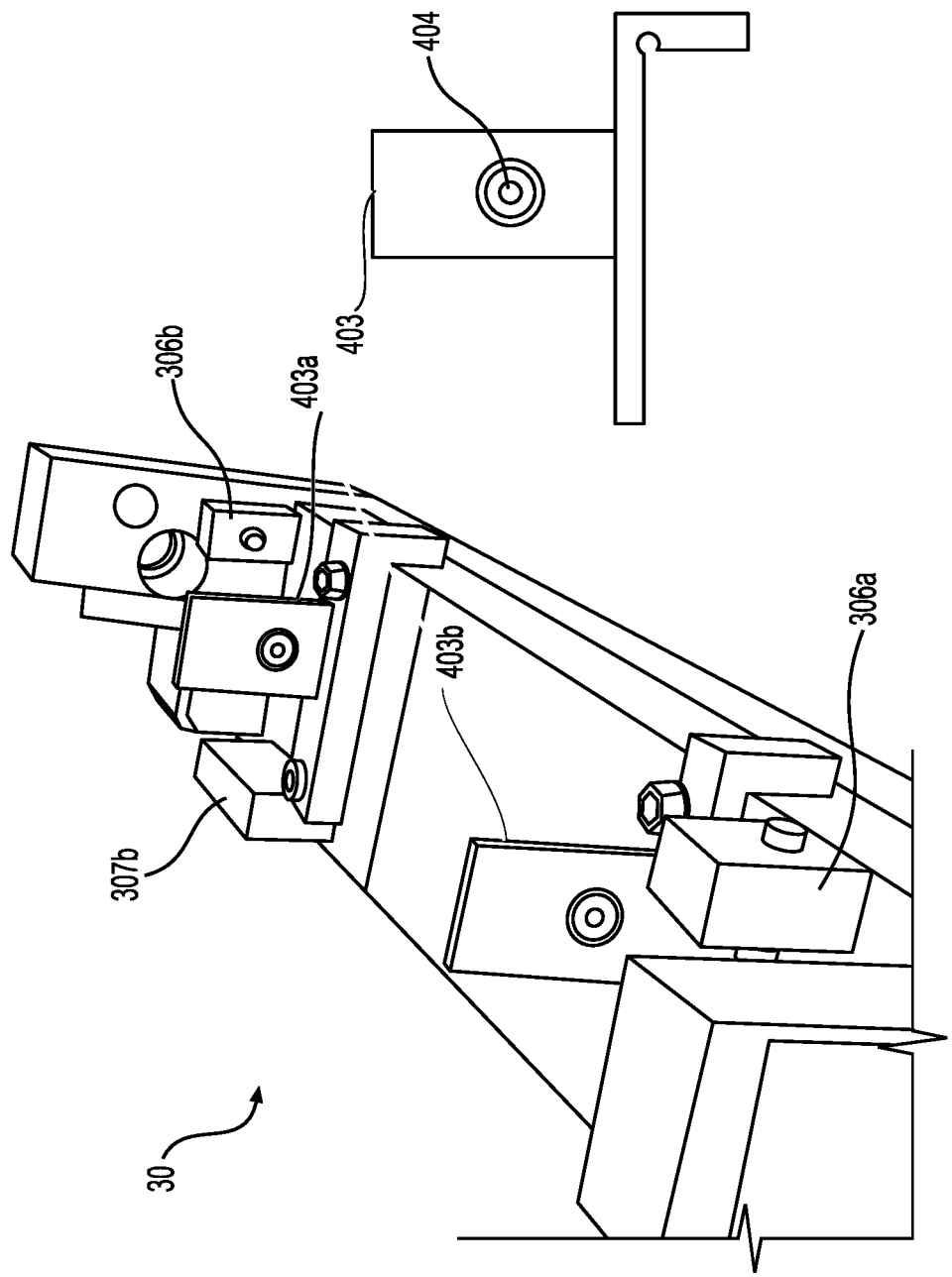
FIG. 5B is a perspective view of a second alignment device according to an exemplary embodiment.

FIGS. 5A and 5B illustrate a second alignment device 403 for assisting in aligning medical laser system 10. Second alignment devices 403 may be positioned within each laser cavity 30 after the CTH:YAG laser rod is removed (FIG. 3A). As shown in FIG. 5B, second alignment devices 403 have an L-shaped base with a body portion extending from the base. As will be described herein, two second alignment devices 403 (a proximal second alignment device 403a and a distal second alignment device 403b) may be used in an alignment procedure. An opening 404 is formed in the body portion of each second alignment device 403 and may allow laser light to pass therethrough during an alignment procedure. A diameter of opening 404 may equal to or greater than approximately 1 mm and less than or equal to approximately 2 mm and a center of opening 404 may be positioned approximately 10 mm to approximately 15 mm from the base of alignment device 403. In some examples, the center of opening 404 may be approximately 12.5 mm from the base of alignment device 403. It will be understood that a diameter of opening 404 in proximal second alignment device 403a may be different than a diameter of opening 404 in distal second alignment device 403b. The L-shaped configuration of alignment device 403 may allow alignment device 403 to be positioned and removably fixed on the top surface of laser cavity 30 via screws or the like. Distal second alignment device 403b is positioned to be flush against a proximal-most surface of distal end wall 306b. Proximal second alignment device 403a is positioned such that a proximal-most surface of proximal second alignment device 403a is flush with a distalmost surface of proximal sidewall 307b.

FIG. 6 illustrates a light source 406 configured to be used to align medical delivery system 10. Light source 406 may include a cable having a distal end 407, the distal end 407 may be configured to be connected to fiber ferrule 107 of alignment apparatus 100 (for example, distal end 407 may include a SMA connector). As will be described herein, an aiming light from light source 406 may be introduced into medical delivery system 10 along light path A to align medical delivery system 10.

Figure 7:
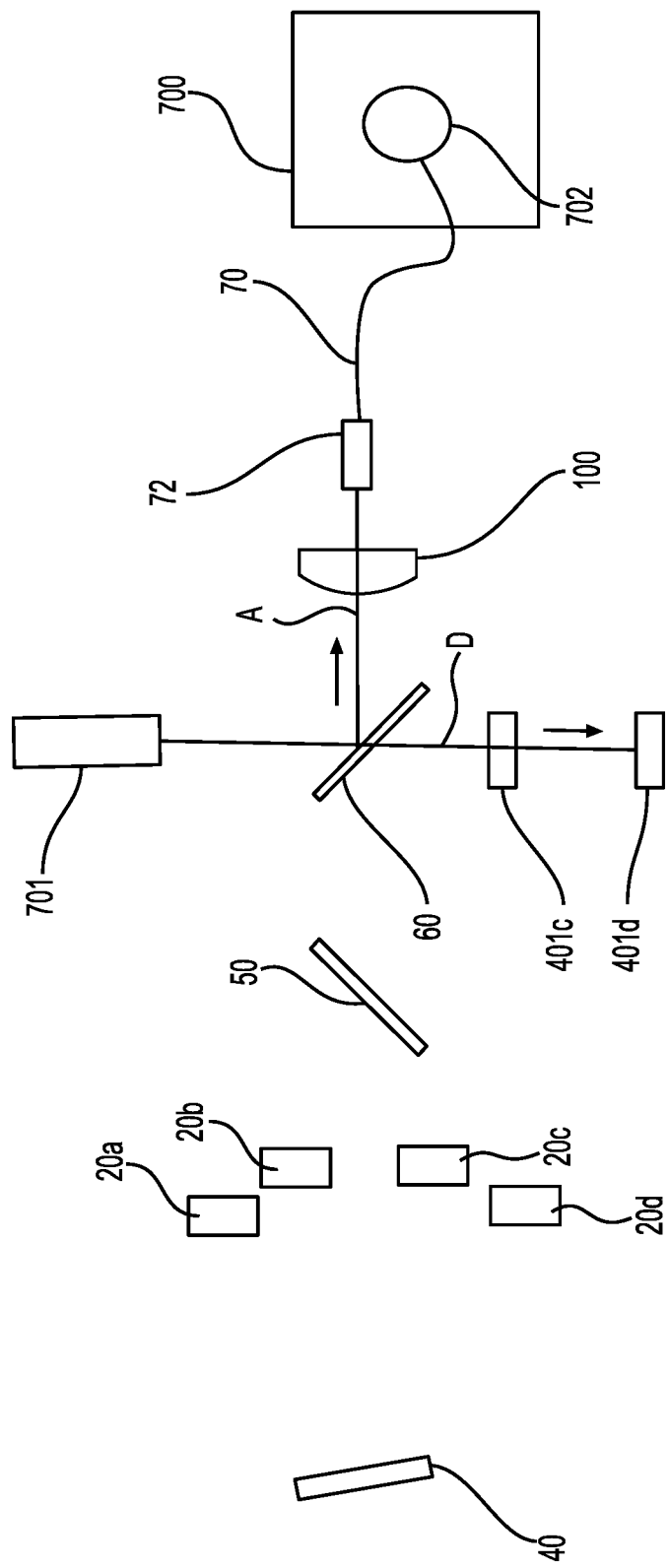
FIG. 7 is a schematic of a third alignment procedure according to an embodiment.

FIG. 7 illustrates an alignment and coupling of a laser guiding beam by medical laser system 10 from an aiming laser source 701. Similar to the laser light from cavities 30a-30d, the aiming laser beam is aligned to ensure the aiming laser beam is properly coupled into fiber 70. A fiber (not shown) connecting aiming laser source 701 to medical laser system 10 may have a diameter of approximately 1 mm and a small divergence. The aiming beam may be a relatively low power light beam in the visual spectrum (approximately 650 nm) that enables an operator to visualize where the output beams from laser cavities 30a-30d may be fired. A portion of aiming light beam may be combined with the output laser by combiner 60 and may travel along laser path A. A portion of the aiming laser beam may also pass through combiner 60 and travel along a laser path D and may assist in alignment of aiming laser source 701. For example, a pair of first alignment devices 401c, 401d, which may be similar to first alignment device 401 shown in FIG. 4, including opening 402, may be positioned along laser path D. As described above, opening 402 may have a diameter equal to or greater than approximately 1 mm and equal to or less than approximately 2 mm, and a diameter of opening 402 in first alignment device 401c may be different from a diameter of first alignment device 401d. As will be described, first alignment devices 401c, 401d may assist in aligning aiming laser source 701.

A method of aligning the medical laser system 10 according to an exemplary embodiment will now be described. At the outset, coordinates of various elements of the medical laser system are described herein, reference for which should be made to FIG. 3.

A first (e.g., initial) alignment procedure according to an exemplary embodiment will now be described. Connector 201 of the aiming laser beam is attached to coupling lens assembly 100 (shown in FIG. 4) via fiber ferrule 107 of coupling lens assembly 100. Alignment devices 401a and 401b are attached to the motherboard of medical laser system 10 along laser path A at positions proximal and distal to mirrors 20a-20d, as shown in FIG. 6. Coupling lens 111 is roughly aligned in the z-direction by moving coupling lens 111 in the z-direction such that the aiming laser beam is collimated along laser beam path A. To move coupling lens 111 in the z-direction, a user rotates adjusting screw 106 (FIG. 2B) in a clockwise and/or a counterclockwise direction. Clockwise movement of adjusting screw 106 may overcome the biasing force of springs 108 and cause base frame 101 to move in the proximal direction. Counterclockwise movement of adjusting screw 106 may allow springs 108 to move or bias base frame 101 in the distal direction. Iterative rotations of adjusting screw 106 in the clockwise and/or counterclockwise direction are performed until the aiming laser beam is collimated along laser path A. The rough alignment of coupling lens 111 in the z-direction may be performed visually, and precise alignment of coupling lens 111 in the z-direction may be performed at a later step, described herein.

Once coupling lens 111 is collimated in the z-direction, adjustment of coupling lens 111 in the x- and y-directions is performed. Adjusting screw 105 may be rotated clockwise and/or counterclockwise to cause lens holder 103 (and coupling lens 111) to move in the x-direction. Adjusting screw 104 may also be rotated in clockwise and/or counterclockwise directions to cause stage plate 102 (and coupling lens 111) to move in the y-direction. Iterative rotations of adjusting screws 104, 105 in clockwise and/or counterclockwise directions is performed until the aiming laser beam passes through openings 402 in each of alignment devices 401a, 401b and impinges on a center of Galvo mirror 40. Once the aiming laser beam impinges on the center of Galvo mirror 40, locking screws 110 are tightened to secure and maintain a position of stage plate 102 and lens holder 103.

Once the aiming laser beam passes through openings 402 in each of alignment devices 401a, 401b and impinges on Galvo mirror 40, such that a distalmost face of Galvo mirror 40 is perpendicular to laser path A. Galvo mirror 40 is subsequently rotated about an x-axis (see FIG. 6) such that the aiming laser beam impinging on Galvo mirror 40 is reflected proximally along laser path A, i.e., back through openings 402 of alignment devices 401a, 401b. Subsequently, minor adjustments may be made in the z-direction via screws 106 and springs 108 to ensure proper alignment of lens 111 in the z-direction. For example, the refractive index between the material of lens 111 and the fiber may cause differences in the focal lengths. Yet, once lens 111 is aligned in the x- and y-directions, minor modifications based on the difference in focal lengths of the laser may be easily achieved.

The refractive beam indexes through coupling lens 111 of the aiming laser beam and the laser generated by laser cavities 30a-30d are different due to the material of coupling lens 111 (e.g., a sapphire material). To ensure a proper output by laser fiber 70, optical lens 111 may be adjusted such that a spot of light formed by the aiming laser beam may be formed at output coupler windows 32a-32d, e.g., on a material placed adjacent each of output coupler windows 32a-32d that may enable a user to view the light spot. The aiming laser beam may be directed into medical laser system 10 as described herein. Coupling lens 111 may be moved along the z-direction via screw 106 and springs 108 until the spot of light is minimized, e.g., a smallest diameter. In other words, for each output coupler window 32a-32d, the position of coupling lens 111 may be moved in the z-direction until the diameter of the spot of light on output coupler windows 32a-32d is smallest, and screws 112 may be tightened to secure coupling lens 111 in the z-direction. In this manner, a position of coupling lens 111 in the z-direction may be secured which may optimize an output of the laser energy from the distal end of laser fiber 70.

A second alignment procedure is performed after the aiming laser beam is used to properly position coupling lens 111. The second alignment procedure ensures alignment of each laser cavity 30a-30d. Laser pumping chamber 308 in FIG. 3A is removed from insulating base plate 305, such that each laser cavity 30 appears as shown in FIG. 3B. Second alignment device 403 is attached to a first laser cavity (e.g., laser cavity 30a) as shown in FIG. 5B. As described herein, one of the second alignment devices 403 is attached such that its proximal-most surface is flush with the distalmost surface of sidewall 307b. Another of the second alignment device 403 is attached such that its distalmost surface is flush against the proximal-most surface of distal end wall 306a. Each of second alignment devices 403 are attached via screws or similar fastening devices to a top surface of insulating base plate 305 (see FIG. 5B). The L-shaped configuration of second alignment devices 403 ensures openings 404 in each of second alignment devices is positioned along laser path C and in a same position as a CTH:YAG laser rod when laser pumping chamber 308 is attached to insulating plate 305, shown in FIG. 5A.

The aiming laser beam is introduced to medical laser system 10 by attaching connector 407 to fiber ferrule 107, as described above. Elements of medical laser system 10 are moved such that the aiming laser beam passes from 407 along laser paths A, B, and C, and such that the aiming laser beam passes through opening 404 in each of second alignment devices 403. To align the aiming laser beam to pass through openings 404, Galvo mirror 40 and first relay mirror 20a are rotated horizontally, e.g. about a y-direction axis, and first relay mirror 20a and first laser cavity 30a are rotated vertically, e.g., about an x-direction axis, as shown in FIG. 5A. Iterative movements of Galvo mirror 40, first relay mirror 20a, and first laser cavity 30a are performed until the aiming laser beam passes through openings 404 in each of second alignment devices 403.

Once the aiming laser beam passes through opening 404 in each of second alignment devices 403, reflecting window 36a and output coupler window 32a are adjusted. Reflecting window 36a is adjusted such that the aiming laser beam is reflected from reflecting window 36a and through opening 404 in the proximal-most second alignment device 403. Reflecting window 36a is adjusted such that the aiming beam reflected from a surface of window 32a passes through opening 402. This is achieved by rotating reflecting window 36a and output coupler window 32a independently of each other horizontally, e.g. about the y-direction axis, vertically, e.g., about the x-direction axis (FIG. 5A).

Once the aiming laser beam reflected from reflecting window 36a passes through opening 404 in the proximal-most second alignment device 403 and the aiming beam is reflected from window 32a through opening 402, the second alignment procedure is performed for all additional laser cavities 30 (e.g., laser cavities 30b-30d) of medical laser system 10. In this manner, laser cavities 30a-30d may be properly aligned.

An alignment check may be performed on medical laser system 10 after laser cavities 30a-30d are properly aligned. A power meter (not shown) may be attached to the output of coupling lens assembly 100 via ferrule 107 via a fiber (e.g., a fiber having a diameter of approximately 910 µm). Laser pumping channels 308 may be reattached to each of laser cavities 30a-30d (FIG. 3A), such that an output laser may be generated. Medical laser system 10 may be operated to generate the output laser energy at several different example energy levels. For example, medical laser system 10 may be operated to generate a low energy output laser, a high energy output laser, and a laser having a large heat dissipation. If the difference in output energy at the power meter for each generated energy level is less than a threshold value (e.g. 5%), the alignment of medical laser system 10 is confirmed.

Once alignment of the output laser is confirmed, optimization of the oscillation of the laser from each laser cavity 30a-30d is performed. A fiber having a diameter of approximately 910 µm may be attached via ferrule 107, and a laser may be generated by each laser cavity and delivered through the fiber (e.g., fiber 70) to an energy sensor. Each mirror 36a-36d may be rotated to maximize the output energy of the laser from each laser cavity 30a-30d. Additional fibers having smaller diameters may subsequently attach the power meter via ferrule 107 to monitor the change of delivered power or pulse energy from medical laser system 10. For example, fibers having diameters of approximately 365 µm and approximately 273 µm may be attached to medical laser system 10 via ferrule 107. The power meter may determine the output power through each of these fibers to ensure the coupling efficiency is with a specific range.

After the optimization of the laser oscillation is complete, an alignment and coupling of a laser guiding beam generated by aiming laser source 701 may be performed using the assembly of FIG. 7. The laser guiding beam may be an aiming beam or the like, and may be a colored beam (e.g., green, red, or the like) to assist a user to perform a medical procedure using the output laser beam. Aiming laser source 701 may be positioned on a mount (not shown) having two-dimensional translation and rotational freedom (e.g., can rotate and translate along the x- and y-axes). Aiming laser source 701 generates the aiming laser onto beam combiner 60, such that the aiming laser enters medical laser system 10 at an angle approximately perpendicular to laser path A. First alignment devices 401(c) and 401(d) may be positioned along laser path D such that openings 402 of each first alignment device 401(c) and 401(d) are positioned along laser path D. A portion of the aiming laser passes through beam combiner. The mount for aiming laser source 701 may be rotated and translated in the x- and y-directions until the aiming laser passing through beam combiner 60 travels along laser path D and through opening 402 in each first alignment device 401(c) and 401(d). Subsequently, connector 72 of output laser fiber 70 is attached to medical laser system 10 via ferrule 107 of assembly 100. A distal end of output laser fiber 70 is aimed at a target 700. If an image 702 (e.g., a light having a color corresponding to the color of the aiming laser beam) is shown on target 700, then the alignment of aiming laser source 701 is confirmed and the aiming laser beam is properly coupled to output laser fiber 70. Additional alignment of aiming laser source 701 may then be performed to optimize the output shape and brightness of the aiming laser beam from the distal end of output laser fiber 70.

Based on the procedures described herein, elements of medical laser system 10 may be properly aligned using an aiming laser beam without the need to generate laser pulses from each laser cavity and delivering the laser pulses to thermal paper. For example, "live" laser pulses generated by the laser cavities may only be necessary for optimizing the resonator oscillation and confirming the beam alignment. Further, the alignment devices provide repeatability and precision to the optomechanical parts and their installation. These devices also provide for improved accuracy over conventional alignment procedures and improve efficiency. Further, the skill required to perform these procedures may be reduced from the skill necessary to perform conventional alignment procedures.

It will be understood that reference is made to a number of cavities and/or mirrors in the medical laser system 10. It will be understood that the devices are not limited to this number and may change according to the requirement of the medical laser system 10. Further, while reference is made to a medical/surgical laser system, the alignment technique described herein is not limited to a medical/surgical laser system and may be used with any laser system.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A laser system, comprising:
a first laser cavity configured to output a laser light along a first path;
a first mirror configured to receive the laser light from the first laser cavity, and redirect the laser light along a second path that is different than the first path;
a second mirror configured to receive the laser light from the first mirror, and redirect the laser light along a third path that is different than the first path and the second path;
a beam splitter located at a first position on the third path;
a beam combiner located at a second position on the third path; and
a coupling lens assembly, the coupling lens assembly including a lens located at a third position on the third path, wherein the coupling lens assembly is configured to move the lens in x-, y-, and x-directions.

2. The laser system according to claim 1, wherein the coupling lens assembly includes an outer housing configured to house:
a base frame;
a stage plate; and
a lens holder configured to support the lens, wherein the base frame, the stage plate, and the lens holder are configured to move relative to each other.

3. The laser system according to claim 2, wherein the stage plate includes a pair of sidewalls, wherein a portion of the lens holder is configured to be disposed between the pair of sidewalls, and wherein the lens holder is configured to move toward one and the other of the pair of sidewalls.

4. The laser system according to claim 3, wherein the base frame includes a top wall and a bottom, wherein a portion of the stage plate is configured to be disposed between the top wall and the bottom wall, and wherein the stage plate is configured to move toward one and the other of the top wall and the bottom wall.

5. The laser system according to claim 2, further including a plurality of screw members configured to move the base frame, the stage plate, and the lens holder.

6. The laser system according to claim 5, further comprising at least one biasing member configured to bias the stage plate in a distal direction.

7. The laser system according to claim 2, further comprising a plurality of locking members configured to lock a position of the base frame, the stage plate, and the lens holder.

8. The laser system according to claim 1, wherein the base frame, the stage plate, and the lens holder are configured to move independently.

9. The laser system according to claim 1, further comprising a plurality of first alignment members, wherein each of the plurality of first alignment members includes an opening, and wherein one first alignment member from the plurality of first alignment members is configured to be disposed on the third path distal to the second mirror, and wherein another first alignment member from the plurality of first alignment members is configured to be disposed on the third path proximal to the second mirror.

10. The laser system according to claim 9, further comprising an aiming laser generator, wherein the aiming laser generator is configured to deliver an aiming laser to the beam combiner, wherein a portion of the aiming laser is configured to pass through the beam combiner along a fourth path, and wherein the aiming laser generator is configured to be aligned when the aiming laser passes through the opening in at least two first alignment members from the plurality of first alignment members arranged on the fourth path.

11. The laser system according to claim 1, further including a pair of second alignment members, each of the second alignment members having an opening, wherein each of the second alignment members are configured to be attached to the first laser cavity on the first path.

12. The laser system according to claim 11, wherein a laser generating rod is configured to be removed from the first laser cavity before the second alignment members are attached to the first laser cavity.

13. The laser system according to claim 12, wherein the laser generating rod is disposed on a first longitudinal axis when the laser generating rod is attached to the first laser cavity, and wherein the opening in each of the second alignment members are disposed on the first longitudinal axis.

14. The laser system according to claim 1, further comprising an output fiber configured to deliver a laser energy from the laser system to a target.

15. The laser system according to claim 1, wherein an alignment laser beam is directed into the laser system from a distalmost end of the third path.

16. A method for aligning a laser system, the method comprising:
delivering an alignment beam through a lens, wherein the lens is supported by a coupling lens assembly; and
adjusting the coupling lens assembly to move the lens in an x-, y-, and z-directions such that the alignment beam passes through an opening in a first alignment feature positioned at a first location and through an opening in a second alignment feature positioned at a second location, onto a first mirror contained within the laser system.

17. The method according to claim 16, further comprising:
removing a laser rod from a laser cavity of the laser system;
attaching a third alignment feature and a fourth alignment feature to the laser cavity, wherein each of the third alignment feature and the fourth alignment feature include an opening;
removing one of the first or second alignment features from the laser system; and
adjusting one or more of the first mirror, a second mirror, and a third mirror such that the alignment beam passes through the openings in both the third alignment feature and the fourth alignment feature, onto a fourth mirror at a proximal end of the laser cavity.

18. The method according to claim 16, further comprising:
adjusting the third mirror, located at a distal end of the laser cavity, and the fourth mirror such that the aiming beam is reflected from the fourth mirror through the opening in one of the third alignment feature or the fourth alignment feature.

19. A method for aligning a laser system having a first laser cavity, the method comprising:
delivering an aiming into the laser system via a lens, wherein the lens is supported by a coupling lens assembly;
moving the lens in one or more of the x-, y-, or z-directions such that the aiming laser impinges on a first mirror; and
moving the first mirror, a second mirror, and a third mirror such that the aiming laser beam passes through openings in a plurality of alignment devices and impinges on a fourth mirror at a proximal end of a laser cavity.

20. The method according to claim 19, further including:
delivering a second aiming laser to the laser system onto a coupler, wherein a first portion of the aiming light passes through the coupler along a first path, and wherein a second portion of the aiming light, different from the first portion, is reflected by the coupler along a second path; and
adjusting a position of the aiming laser such that the first portion of the aiming light passes through openings in a pair of alignment devices disposed along the first path.

* * * * *